(12) United States Patent
Lee et al.

(10) Patent No.: US 12,672,782 B2
(45) Date of Patent: Jul. 7, 2026

(54) APPARATUS AND METHOD FOR ESTIMATING BODY TEMPERATURE

(71) Applicants: SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Ho Taik Lee, Yongin-si (KR); Woochul Kim, Seoul (KR); Sang Kyu Kim, Yongin-si (KR); Bok Soon Kwon, Seoul (KR); Jiyong Kim, Seoul (KR); So Young Lee, Suwon-si (KR); Gimin Park, Hanam-si (KR); Seungjai Woo, Seoul (KR)

(73) Assignees: SAMSUNG ELECTRONICS CO., LTD., Suwon-si (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 687 days.

(21) Appl. No.: 18/077,000

(22) Filed: Dec. 7, 2022

(65) Prior Publication Data

US 2023/0248246 A1 Aug. 10, 2023

(30) Foreign Application Priority Data

Feb. 8, 2022 (KR) ........................ 10-2022-0016008

(51) Int. Cl.
*A61B 5/01* (2006.01)
*A61B 5/00* (2006.01)
*A61B 5/024* (2006.01)

(52) U.S. Cl.
CPC ............ *A61B 5/01* (2013.01); *A61B 5/02416* (2013.01); *A61B 5/681* (2013.01)

(58) Field of Classification Search
CPC ....... A61B 5/01; A61B 5/02416; A61B 5/681; A61B 5/02108; A61B 5/026;
(Continued)

(56) References Cited

U.S. PATENT DOCUMENTS 6,138,079 A * 10/2000 Putnam .................. G16H 10/20
702/50
8,716,629 B2 5/2014 Klewer et al.
(Continued)

FOREIGN PATENT DOCUMENTS

JP 2018021833 A * 2/2018
JP 2019-55087 A 4/2019
(Continued)

OTHER PUBLICATIONS

Hashimoto JP-2018021833-A (English Translation) (Year: 2018).*
(Continued)

*Primary Examiner* — Adam J Eiseman
*Assistant Examiner* — Lucy Eppert
(74) *Attorney, Agent, or Firm* — Sughrue Mion, PLLC

(57) ABSTRACT

An apparatus for estimating body temperature includes: a first temperature sensor configured to measure surface temperature of a wrist of a user; and a processor configured to calculate skin heat flux based on the surface temperature of the wrist, to estimate central wrist temperature of the user based on the surface temperature of the wrist, the calculated skin heat flux, and a blood flow rate and metabolism of the user, and to estimate core body temperature of the user based on the estimated central wrist temperature.

19 Claims, 11 Drawing Sheets

(58) Field of Classification Search
CPC ... A61B 5/4866; A61B 5/6833; A61B 5/7275;
A61B 2560/0223
See application file for complete search history.

(56) References Cited

U.S. PATENT DOCUMENTS

| | | | |
|---|---|---|---|
| 9,354,122 | B2 | 5/2016 | Bieberich et al. |
| 9,699,546 | B2 | 7/2017 | Qian et al. |
| 9,716,937 | B2 | 7/2017 | Qian et al. |
| 9,734,833 | B2 | 8/2017 | Disch et al. |
| 10,088,373 | B2 | 10/2018 | Durrer et al. |
| 10,152,978 | B2 | 12/2018 | Disch et al. |
| 10,209,209 | B2 | 2/2019 | Ikeda et al. |
| 10,258,280 | B2 | 4/2019 | Justice et al. |
| 10,274,383 | B2 | 4/2019 | Bieberich et al. |
| 10,278,592 | B2 | 5/2019 | Fish et al. |
| 10,405,755 | B2 | 9/2019 | Shrubsole et al. |
| 10,668,206 | B2 | 6/2020 | Newell et al. |
| 10,765,409 | B2 | 9/2020 | Lafon et al. |
| 10,959,942 | B2 | 3/2021 | Sandvang et al. |
| 11,051,700 | B2 | 7/2021 | Koch et al. |
| 11,071,814 | B2 | 7/2021 | Newell et al. |
| 11,090,423 | B2 | 8/2021 | Newell et al. |
| 11,090,424 | B2 | 8/2021 | Newell et al. |
| 11,253,508 | B2 | 2/2022 | Finck et al. |
| 2007/0225614 | A1 | 9/2007 | Naghavi et al. |
| 2016/0331244 | A1* | 11/2016 | Barton-Sweeney ..... A61B 5/01 |
| 2019/0298708 | A1 | 10/2019 | Jain |
| 2020/0060869 | A1 | 2/2020 | Telfort et al. |
| 2020/0217727 | A1 | 7/2020 | Heitz et al. |
| 2021/0353842 | A1 | 11/2021 | Newell et al. |
| 2022/0042856 | A1 | 2/2022 | Igawa et al. |
| 2023/0099531 | A1* | 3/2023 | Tadele .................... G01K 7/02 374/30 |

FOREIGN PATENT DOCUMENTS

| | | | |
|---|---|---|---|
| JP | 2021-162453 | A | 10/2021 |
| KR | 10-2010-0019084 | A | 2/2010 |
| KR | 10-1123085 | B1 | 3/2012 |
| KR | 10-2015-0056875 | A | 5/2015 |
| KR | 10-1615179 | B1 | 4/2016 |
| KR | 10-2016-0126172 | A | 11/2016 |
| KR | 10-1779837 | B1 | 9/2017 |
| KR | 10-2020-0036808 | A | 4/2020 |
| KR | 10-2147080 | B1 | 8/2020 |
| KR | 10-2021-0072108 | A | 6/2021 |
| WO | 2017/001701 | A1 | 1/2017 |
| WO | 2017/062923 | A1 | 4/2017 |

OTHER PUBLICATIONS

University of Minnesota, Atlas of Human Cardiac Anatomy, Physiology Tutorial—Blood Flow, 2021 (Year: 2021).*
J. Werner et al., "Temperature profiles with respect to inhomogeneityand geometry of the human body", J Appl Physiol (1985), 1 Page, https://pubmed.ncbi.nlm.nih.gov/3182480/.
K.H. Wesseling et al., "Computation of aortic flow from pressure in humans using a nonlinear, three-element model", Modeling in Physiology, 1993, 8 Pages.
Carol Elaine Smith "A Transient, Three-Dimensional Model of the Human Thermal System", UMI, 1991, 24 Pages.

* cited by examiner

640a

APPARATUS AND METHOD FOR ESTIMATING BODY TEMPERATURE

CROSS-REFERENCE TO RELATED APPLICATION(S)

This application claims priority from Korean Patent Application No. 10-2022-0016008, filed on Feb. 8, 2022 in the Korean Intellectual Property Office, the disclosure of which is incorporated herein by reference in its entirety.

BACKGROUND

1. Field

The following description relates to an apparatus and method for estimating body temperature of a user.

2. Description of the Related Art

Generally, body temperature is one of the four main vital signs and has very important clinical significance. A body temperature sensor may be used in various applications, such as checking infections in patients, thermal side effects of medications, or time of ovulation in women, and the like. However, the skin temperature and core body temperature may vary depending on external temperature, such that it is difficult to measure the core body temperature by using a portable device such as a wearable device. A general body temperature sensor may be classified into a contact type sensor and a non-contact type sensor. Examples of the contact type sensor may include a sensor for detecting a change in electrical resistance, such as a Resistance Temperature Detector (RTD), a thermistor, etc., a thermocouple for detecting electromotive force, and the like. Further, examples of the non-contact type sensor may include a thermopile, a micro-bolometer, and the like, which measure body temperature by detecting infrared rays radiating from a body surface. A general body temperature measuring technology is greatly affected by a change in environment factors affecting heat transfer, such as a change in external ambient temperature, humidity, air flow, and the like.

SUMMARY

According to an aspect of an example embodiment, an apparatus for estimating body temperature may include: a first temperature sensor configured to measure a skin surface temperature at a measurement point of a user; and a processor configured to: calculate skin heat flux based on the skin surface temperature, estimate a centroid temperature at the measurement point of the user based on the skin surface temperature at the measurement point, and the calculated skin heat flux, and estimate a core body temperature of the user based on the estimated centroid temperature at the measurement point.

The apparatus may further include: a second temperature sensor; and a thermally conductive material that is disposed between the first temperature sensor and the second temperature sensor, wherein the second temperature sensor may be configured to measure a surface temperature of the thermally conductive material.

At least one of the first temperature sensor and the second temperature sensor is a thermistor.

The processor may be further configured to calculate the skin heat flux by subtracting the surface temperature of the thermally conductive material, from the skin surface temperature at the measurement point of the user.

The apparatus may further include a photoplethysmography (PPG) sensor configured to measure a PPG signal from the user. The processor may be further configured to estimate blood pressure of the user based on the measured PPG signal, estimate a blood flow rate of the user based on the estimated blood pressure, and estimate the centroid temperature at the measurement point of the user further based on the blood flow rate of the user.

The processor may be further configured to estimate an amount of heat that is released from a body of the user based on at least one of a heart rate, an age, a stature, and a weight of the user.

The processor may be further configured to estimate the centroid temperature at the measurement point of the user based further on thermal conductivity of a skin tissue of the user, and a radius of a body part at the measurement point of the user.

The measurement point may be located at a wrist of the user, and the processor may be further configured to estimate the core body temperature based on a length of an arm of the user, the centroid temperature of the wrist, a heat flux in the wrist, an arterial blood pressure, and a blood flow rate.

The processor may be further configured to calculate the heat flux in the wrist based on a convection coefficient of blood, a mean temperature of blood, and a temperature of a blood vessel wall.

The apparatus may further include a display configured to provide the user with the estimated core body temperature of the user.

The measurement point is a first measurement point, and the apparatus may further include a third temperature sensor configured to measure a skin surface temperature at a second measurement point of the user, wherein the processor may be configured to estimate the core body temperature further based on the skin surface temperature at the second measurement point of the user.

The processor may be configured to estimate the core body temperature further based on an ambient air temperature.

According to another aspect of an example embodiment, a wearable device configured to be worn around a wrist of a user, may include: a first contact-type temperature sensor and a second contact-type temperature that are disposed apart from each other, via a thermally conductive layer provided between the first contact-type temperature sensor and the second contact-type temperature; and a processor configured to: control the first contact-type temperature sensor to measure a skin surface temperature of the wrist; control the second contact-type temperature sensor to measure a temperature of the thermally conductive layer; calculate a skin heat flux based on change between the skin surface temperature of the wrist and the temperature of the thermally conductive layer; estimate a centroid temperature of the wrist based on the skin surface temperature of the wrist and the skin heat flux, and estimate a core body temperature of the user based on the centroid temperature of the wrist, and a length of an arm of the user.

According to another aspect of an example embodiment, a method of estimating body temperature may include: measuring a skin surface temperature at a measurement point of a user; calculating skin heat flux based on the skin surface temperature; estimating a centroid temperature at the measurement point based on the skin surface temperature at the measurement point, and the calculated skin heat flux; and estimating a core body temperature of the user based on the estimated centroid temperature at the measurement point.

The skin surface temperature is measured by a first temperature sensor, and the method further may include measuring, by a second temperature sensor, a surface temperature of a thermally conductive material that is provided between the first temperature sensor and the second temperature sensor, and the calculating of the skin heat flux may include calculating the skin heat flux by subtracting the surface temperature of the thermally conductive material from the skin surface temperature.

The estimating of the centroid temperature at the measurement point may include: measuring a photoplethysmography (PPG) signal from the user; estimating blood pressure of the user based on the measured PPG signal; estimating a blood flow rate based on the estimated blood pressure of the user, and estimating the centroid temperature further based on the blood flow rate.

The estimating of the centroid temperature at the measurement point may include estimating an amount of heat that is released from a body of the user based on at least one of a heart rate, an age, a stature, and a weight of the user.

The estimating of the centroid temperature at the measurement point may include estimating the centroid temperature at the measurement point based further on thermal conductivity of a skin tissue of the user and a radius of a body part at the measurement point of the user.

The measurement point may be located at a wrist of the user, and the estimating of the core body temperature of the user may include estimating the centroid temperature of the wrist based on a length of an arm of the user, the centroid temperature of the wrist, a heat flux in the wrist, an arterial blood pressure, and a blood flow rate.

The estimating of the core body temperature of the user comprises calculating the heat flux in the wrist based on a convection coefficient of blood, a mean temperature of blood, and a temperature of a blood vessel wall.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
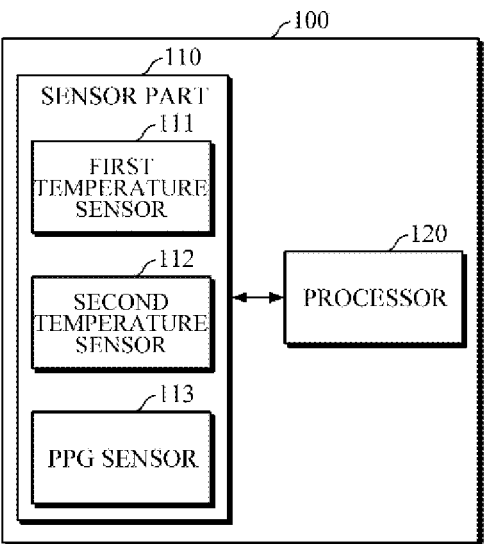
FIG. 1 is a block diagram illustrating an apparatus for estimating body temperature according to an example embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for estimating body temperature according to an example embodiment of the present disclosure. An apparatus 100 for estimating body temperature may be mounted in various electronic devices. Examples of the electronic device may include a cellular phone, a smartphone, a tablet PC, a laptop computer, a personal digital assistant (PDA), a portable multimedia player (PMP), a navigation device, an MP3 player, a digital camera, a wearable device, etc., and examples of the wearable device may include a wristwatch-type wearable device, a wristband-type wearable device, an earphone-type wearable device, a ring-type wearable device, a waist belt-type wearable device, a necklace-type wearable device, an ankle band-type wearable device, a thigh band-type wearable device, a forearm band-type wearable device, and the like. However, the electronic device and the wearable device are not limited to the above examples.

Referring to FIG. 1, the apparatus 100 for estimating body temperature may include a sensor part 110 and a processor 120.

The sensor part 110 may obtain data for estimating core body temperature from an object. The term "object" may refer to a user, a body part of the user, or an area on a wrist that is adjacent to an radial artery and an area on an upper part of the wrist where venous blood or capillary blood passes. However, the object is not limited thereto, and may be a peripheral part of the human body, such as a finger, a toe, or the like, where blood vessels are densely distributed in the human body.

The sensor part 110 may measure surface temperature of a user's wrist.

For example, the sensor part 110 may include a first temperature sensor 111 for measuring the surface temperature of the user's wrist. The first temperature sensor 110 may include a thermistor, but is not limited thereto. The thermistor may be a contact type temperature sensor among temperature sensors for measuring temperature.

In another example, the sensor part may further include an electrocardiogram (ECG) sensor, which may measure the surface temperature of the user's wrist by converting an electrical resistance value of ECG electrodes into a temperature value. In this case, the ECG sensor may include a plurality of electrodes.

The processor 120 may be electrically connected to the sensor part 110, and may control the sensor part 110 during estimation of a user's core body temperature. The processor 120 may estimate the user's core body temperature based on the data obtained by the sensor part 110.

For example, the processor 120 may estimate a user's central wrist temperature and may estimate the user's core body temperature based on the measured central wrist temperature. In particular, based on the data obtained by the sensor part 110, the processor 120 may calculate skin heat flux at the user's wrist, which is used as a reference for estimating the core body temperature, and/or may estimate a user's blood flow rate, heat release from metabolism in the human body, and the like.

The sensor part 110 may include a second temperature sensor 112, and the processor 120 may calculate the skin heat flux at the user's wrist based on temperature measurement results of the first temperature sensor 111 and the second temperature sensor 112.

The first temperature sensor 111 and the second temperature sensor 112 may include a thermistor. In particular, the first temperature sensor 111 and the second temperature sensor 112 may form a thermistor pair with a thermally conductive material disposed therebetween.

An arrangement of the first temperature sensor 111 and the second temperature sensor 112, and a process of calculating the skin heat flux at the user's wrist by the processor 120 based on the temperature measurement results of the first temperature sensor 111 and the second temperature sensor 112 will be described below with reference to FIG. 2.

Figure 2:
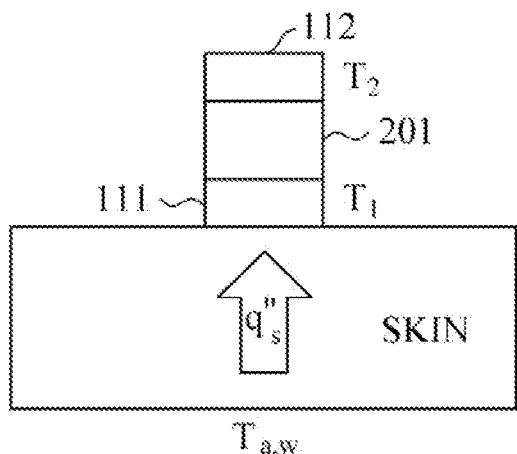
FIG. 2 is a diagram illustrating an arrangement of a first temperature sensor and a second temperature sensor according to an example embodiment of the present disclosure.

FIG. 2 is a diagram illustrating an arrangement of the first temperature sensor and the second temperature sensor.

Referring to FIG. 2, the second temperature sensor 112 may be disposed at an upper end of a thermally conductive material 201 which is disposed at an upper end of the first temperature sensor 111. That is, the thermally conductive material 201 may be disposed between the first temperature sensor 111 and the second temperature sensor 112. The first temperature sensor 111 is configured to be in contact with a skin surface during a temperature measurement, whereas the second temperature sensor 112 is configured to be apart from the skin surface. In particular, the first temperature sensor 111 and the second temperature sensor 112 may be formed in a stacked structure with the thermally conductive material 201 being disposed therebetween.

The first temperature sensor 111 may be disposed at a lower end of the thermally conductive material 201 to measure surface temperature of a user's wrist, and the second temperature sensor 112 may be disposed at an upper end of the thermally conductive material 201 to measure surface temperature of the thermally conductive material 201.

In particular, the thermally conductive material 201 may be, for example, an insulator having a size of 0.1 mm to 5 mm and may be a material (e.g., polyurethane foam) having a thermal conductivity of 0.1 W/mK or less. The size and thermal conductivity of the insulator are not limited thereto. Further, an air-filled structure may also be provided in which air having a very low thermal conductivity is filled between the first temperature sensor 111 and the second temperature sensor 112, without using a separate material therebetween.

The processor 120 may calculate skin heat flux of a user based on a temperature measurement result of the first temperature sensor 111 and a temperature measurement result of the second temperature sensor 112. For example, the processor 120 may calculate the skin heat flux of the user in real time during the temperature measurement of the first temperature sensor 111 and the second temperature sensor 112, based on a value obtained by subtracting, from the surface temperature of the user's wrist, which is measured by the first temperature sensor 120, the surface temperature of the thermally conductive material 201 which is measured by the second temperature sensor 112.

Referring to FIG. 2, the processor 120 may calculate skin heat flux $q''_s$ based on a temperature difference $T_1$-$T_2$ between a surface temperature $T_1$ of the user's wrist, which is measured by the first temperature sensor 111, and a surface temperature $T_2$ of the thermally conductive material 201 which is measured by the second temperature sensor 112. In particular, the processor 120 may calculate the skin heat flux at the user's wrist by using the following Equation 1, but is not limited thereto.

$$q''_s = (T_1 - T_2)/R''_{sensor} \qquad \text{[Equation 1]}$$

$$R''_{sensor} = t_{sensor}/k_{sensor}$$

Herein, $q''_s$ denotes the skin heat flux; $T_1$ denotes the surface temperature of the user's wrist, which is measured by the first temperature sensor 111; $T_2$ denotes the surface temperature of the thermally conductive material 201, which is measured by the second temperature sensor 112; $R''_{sensor}$ denotes a thermal resistance value of the thermally conductive material 201; $t_{sensor}$ denotes the thickness (mm) of the thermally conductive material 201; and $k_{sensor}$ denotes the thermal conductivity (W/mK) of the thermally conductive material 201.

In an embodiment of the present disclosure, the second temperature sensor 112 may be omitted, and the sensor part 110 may include a separate heat flux sensor (HFS) instead of the second temperature sensor 112. In this case, the processor 120 may estimate the user's central wrist temperature based on a heat flux measurement result of the heat flux sensor. The heat flux sensor may have various shapes and types, such as Layered gauge, Gardon gauge, and the like.

Referring back to FIG. 1, the sensor part 110 may include a photoplethysmography (PPG) sensor 113, and may estimate a user's blood flow rate based on a PPG signal measurement result of the PPG sensor 113.

The PPG sensor 113 may include a light source for emitting light onto an object (e.g., a user's wrist), and a detector for detecting emanating light scattered or reflected from body tissue of the user's wrist after light is emitted by the light source onto the object. In particular, the light source may include at least one of a light emitting diode (LED), a laser diode (LD), a phosphor, etc., but is not limited thereto. There may be one or more light sources. For example, the light source may include an LED array. The detector may include a photodiode, a photo transistor, a photodiode array, a phototransistor array, an image sensor (e.g., complementary metal-oxide semiconductor (CMOS) image sensor), and the like.

The PPG sensor 113 may further include one or more additional components required for measuring a PPG signal. For example, the PPG sensor 113 may further include an amplifier for amplifying an electrical signal output by the detector that detects light, an analog-to-digital converter for converting an analog electrical signal, output by the detector or the amplifier, into a digital signal, and the like.

The processor 120 may estimate a user's blood flow rate based on the PPG signal measured by the PPG sensor 113. For example, the processor 120 may estimate a user's cardiac output based on the measured PPG signal, and may estimate the user's blood flow rate based on the estimated cardiac output.

For example, the processor 120 may estimate a user's blood pressure based on a feature related to blood pressure and extracted from the measured PPG signal, and using a predefined blood pressure estimation model, and may estimate the user's cardiac output based on the estimated blood pressure. In particular, the processor 120 may estimate the user's cardiac output based on the following Equation 2, which is a differential equation.

$$\left(1 + \frac{R_c}{R_a}\right)Q(t) + C_a R_a \frac{dQ(t)}{dt} = \frac{P(t)}{R_a} + C_a \frac{dP(t)}{dt} \qquad \text{[Equation 2]}$$

Herein, P(t) denotes the user's blood pressure; Q(t) denotes the cardiac output; $R_c$ denotes aortic impedance; $R_a$ denotes resistance of the artery; and $C_a$ denotes aorta elasticity. In this case, $R_c$, $R_a$, and $C_a$ may be calculated by a known equation using a cross sectional area of the aorta, aorta elasticity per unit length, a user's gender, age, etc., as variables of the equation.

Upon estimating the cardiac output, the processor 120 may estimate the user's blood flow rate based on the estimated cardiac output. The cardiac output of blood, leaving the heart into the aorta, is distributed throughout the body, and the skin receives about 5% and muscles receive about 15% of the cardiac output at rest. Based on such characteristics, the processor 120 may estimate a user's blood flow rate by using an equation that defines a relationship between the cardiac output and the blood flow rate.

In an embodiment of the present disclosure, the PPG sensor 113 may be omitted, and the apparatus 100 for estimating body temperature may receive the user's blood flow rate, measured by an external device, through a communication interface that communicates with the external device, or may receive the blood flow rate previously input by the user.

The processor 120 may estimate heat release from metabolism of the user's body based on the user's heart rate, age, stature, weight, and the like.

For example, the processor 120 may estimate the user's metabolism based further on heart rate along with age, stature, and weight. In particular, the processor 120 may estimate the user's metabolism by using heart rate input by the user or heart rate received from the external device, or by extracting heart rate from the PPG signal measured by the PPG sensor included in the sensor part 110.

The processor 120 may estimate heat release from metabolism of the user's body based on an equation using Equivalent metabolic rate, Maximum Work Capacity (MWC), metabolic rate at rest, mean value of heart rate, a user's gender, age, stature, weight, etc., as variables.

In another example, the processor 120 may estimate a user's basal metabolic rate by using an equation for estimating the user's basal metabolic rate based on the user's age, stature, and weight. In particular, the processor 120 may estimate the heat release from the user's metabolism based on a value obtained by multiplying the estimated basal metabolic rate by a predetermined constant value according to a user's activity level, e.g., number of times of exercise, moving distance, and the like.

However, unlike the above example, the processor 120 may receive a user's metabolism, estimated by an external device, through a communication interface or may receive the user's metabolism previously input by the user.

The processor 120 may estimate a user's central wrist temperature based on the surface temperature of the user's wrist, and may estimate core body temperature of the user based on the estimated central wrist temperature, which will be described in detail below with reference to FIG. 3.

Figure 3:
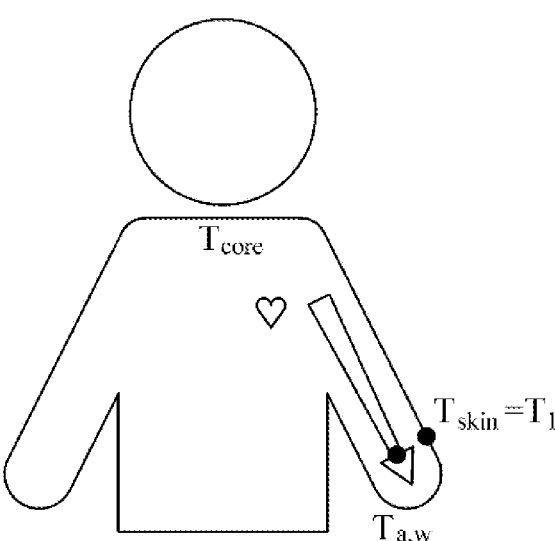
FIG. 3 is a diagram explaining wrist surface temperature, central wrist temperature, and core body temperature of a user according to an example embodiment of the present disclosure.

FIG. 3 is a diagram explaining wrist surface temperature, central wrist temperature, and core body temperature of a user. The term "central wrist temperature" may refer to a temperature at the centroid, the center of mass, or the center of gravity of the wrist.

A user's core body temperature may be defined as an internal body temperature near a person's heart, for example a pulmonary artery temperature when blood is pumped out of a person's heart. In case of the blood is pumped out of the heart, heat loss may occur while the blood flows from the heart to the artery in the wrist. When core body temperature $T_s$ is estimated non-invasively based on the wrist surface temperature $T_1$ and skin heat flux by using a simple conductive heat transfer model from the core to the skin ($T_{core} \rightarrow T_{skin}$), the heat loss may not be reflected, leading to low accuracy in estimating body temperature. Accordingly, by using a two-stage heat transfer model for heat transfer from the core of the body to the centroid of the wrist ($T_{core} \rightarrow T_{a,w}$) and heat transfer from the centroid of the wrist to the skin surface of the wrist ($T_{a,w} \rightarrow T_{skin}$), the core body temperature may be estimated with improved accuracy.

Referring back to FIG. 1, the processor 120 may estimate the central wrist temperature $T_{a,w}$ by using the following Equation 3, but is not limited thereto.

$$T_{a,w} = \frac{k\left(T_s \cdot a - \sqrt{a} \cdot q_s'' \times \frac{I_0(\sqrt{a} \cdot R)}{I_1(\sqrt{a} \cdot R)}\right) - q_m'''}{\omega \cdot \rho_b \cdot c_{p,b}} \qquad \text{[Equation 3]}$$

$$a = \frac{\omega \cdot \rho_b \cdot c_{p,b}}{k}$$

Herein, k denotes thermal conductivity of a user's wrist tissue and may be a predetermined value commonly defined for a plurality of users, or may be a value defined differently according to an individual user's characteristics. In this case, the user's wrist tissue may include muscles, fat, bones, skin, and the like of the wrist. $T_s$ denotes surface temperature of the user's wrist; $q''_s$ denotes heat flux of the wrist; R denotes a radius of the user's wrist and a value input from the user, $q''_m$ denotes heat release from metabolism; $\omega$ denotes blood flow rate; $\rho_b$ denotes blood density; $C_{p,b}$ denotes specific heat at constant pressure of blood and may be a predetermined value commonly defined for a plurality of users; and $I_0(\sqrt{a}\cdot R)$ and $I_1(\sqrt{a}\cdot R)$ denote a Bessel function which is a solution of a heat transfer differential equation.

The processor 120 may estimate a user's core body temperature based on the estimated central wrist temperature of the user.

For example, based on the user's central wrist temperature, the processor 120 may estimate the core body temperature according to distance from the user's wrist, which will be described below with reference to FIG. 4.

Figure 4:
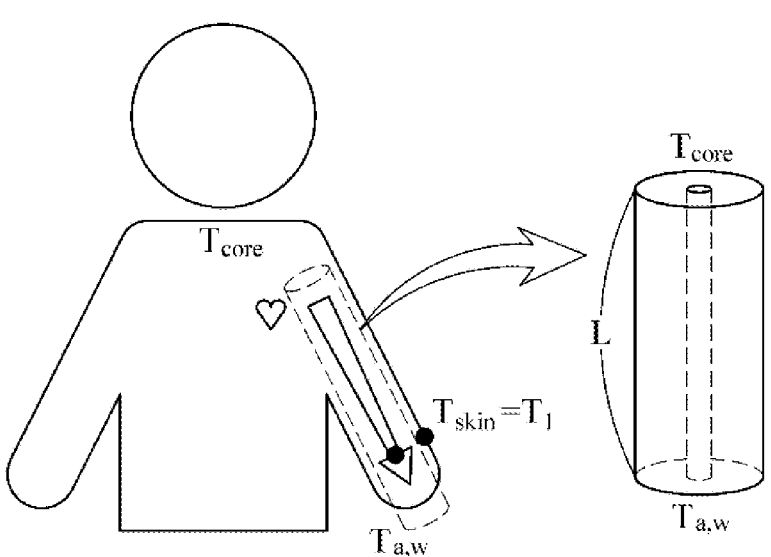
FIG. 4 is a diagram explaining an example of estimating core body temperature according to distance from the wrist.

FIG. 4 is a diagram explaining an example of estimating core body temperature according to distance from the wrist.

Referring to FIG. 4, L denotes a distance from the wrist to the upper arm of a user (e.g., a length of an arm), $T_{a,w}$ denotes the user's central wrist temperature, and $T_{core}$ denotes the user's core body temperature. The value of L may be input by the user, or may be calculated by the processor 120 based on a user profile, including a height and a gender.

In particular, the processor 120 may estimate the core body temperature ($T_a(z)$) according to distance z from the user's wrist by using the following Equation 4.

$$T_a(z) = T_{a,w} + \frac{q''_{a,w} \cdot P_{artery}}{\dot{m}_{blood} \cdot c_{p,b}} \cdot z \qquad \text{[Equation 4]}$$

$$q''_{a,w} = h_{blood}(T_{mean,blood} - T_{wall,blood})$$

Herein, $T_{a,w}$ denotes the user's estimated central wrist temperature; $q''_{a,w}$ denotes heat flux in the user's wrist; $P_{artery}$ denotes the user's arterial pressure; $\dot{m}_{blood}$ denotes flow of mass m through a surface per unit time t and may be a predetermined value commonly defined for a plurality of users; $c_{p,b}$ denotes specific heat at constant pressure of blood as shown in Equation 6; $h_{blood}$ denotes convection coefficient of blood and may be a predetermined value commonly defined for a plurality of users; $T_{mean,blood}$ denotes mean temperature of blood; and $T_{wall,blood}$ denotes temperature of the blood vessel wall.

The mean temperature of blood $T_{mean,blood}$ and the temperature of the blood vessel wall $T_{wall,blood}$ may be calculated by the following Equation 5, but the calculation is not limited thereto.

$$T_{mean,blood} = T_s + q''_s \cdot \frac{I_0(\sqrt{a} \cdot R)}{I_1(\sqrt{a} \cdot R)} \cdot \frac{1}{k\sqrt{a}} - \frac{q'''_m}{ka} \qquad \text{[Equation 5]}$$

$$a = \frac{\omega \cdot \rho_b \cdot c_{p,b}}{k}$$

$$T(r) = T_{mean,blood} + \frac{q'''_m}{\omega \cdot \rho_b \cdot c_{p,b}} + \frac{I_0(\sqrt{a} \cdot r)}{I_0(\sqrt{a} \cdot R)} \cdot \left(T_s - T_{a,w} - \frac{q'''_m}{\omega \cdot \rho_b \cdot c_{p,b}}\right)$$

$$T_{wall,blood} = T(r)_{r=0}$$

As described above, $T_{mean,blood}$ denotes the mean temperature of blood; and $T_{wall,\ blood}$ denotes the temperature of the blood vessel wall. Assuming that the blood vessels are located in the central portion of the wrist, the mean temperature of blood and the temperature of the blood vessel wall may be calculated by substituting a value of zero for r in the function of $T(r)$. Other parameters are described above in Equation 3.

In particular, as illustrated in FIG. 4, a distance from the user's wrist to the upper arm is L, such that by substituting L into a value of z in Equation 4, the core body temperature of the upper arm may be estimated. However, the estimation is not limited thereto, and by substituting an arbitrary constant x for the value of z in Equation 4, the core body temperature at a distance x from the user's wrist may be estimated.

Figure 5:
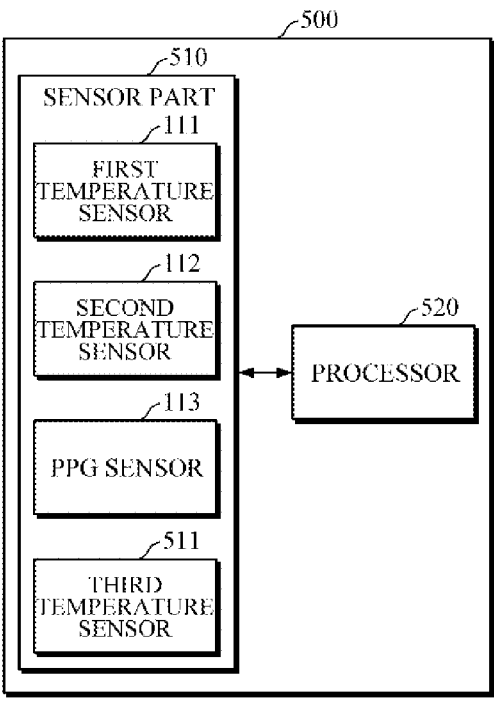
FIG. 5 is a block diagram illustrating an apparatus for estimating body temperature according to another example embodiment of the present disclosure.

FIG. 5 is a block diagram illustrating an apparatus for estimating body temperature according to another example embodiment of the present disclosure.

Referring to FIG. 5, an apparatus 500 for estimating body temperature includes a sensor part 510 and a processor 520.

The sensor part 510 may obtain data for estimating core body temperature from an object.

The sensor part 510 may include the first temperature sensor 111, the second temperature sensor 112, the PPG sensor 113, and a third temperature sensor 511. The first temperature sensor 111, the second temperature sensor 112, and the PPG sensor 113 are described above with reference to FIG. 1, such that a description thereof will be omitted.

The third temperature sensor 511 comes into contact with a user's upper arm to measure surface temperature of the user's upper arm. In this case, the third temperature sensor 510 may be a patch type temperature sensor, but is not limited thereto.

The processor 520 may be electrically connected to the sensor part 510 and may control the sensor part 510 during estimation of the user's core body temperature.

The processor 520 may estimate the user's core body temperature based on the data obtained by the sensor part 110. In particular, the processor 520 may calculate skin heat flux at the user's wrist, which is used as a reference for estimating the user's core body temperature, and/or may estimate a user's blood flow rate, heat release from metabolism in the human body, and the like.

Based on the surface temperature of the user's upper arm, which is measured by the third temperature sensor 511, the processor 50 may estimate the user's core body temperature $T_{core}$ by using the following Equation 6. However, the estimation is not limited thereto. Here, it may be assumed that the user's core body temperature $T_{core}$ is arterial temperature of the user's upper arm.

$$T_{core} = \frac{k\left(T_{s,upper\ arm} \cdot a - \sqrt{a} \cdot h_{eff} \cdot \frac{(T_{s,upper\ arm} - T_\infty) \times \frac{I_0(\sqrt{a} \cdot R)}{I_1(\sqrt{a} \cdot R)}\right) - q'''_m}{\omega \cdot \rho_b \cdot c_{p,b}} \qquad \text{[Equation 6]}$$

$$a = \frac{\omega \cdot \rho_b \cdot c_{p,b}}{k}$$

$$h_{eff} = h_{convection} + h_{radiation} + h_{evaporation} = \frac{q''_s}{T_{s,upper\ arm} - T_\infty}$$

In this case, k denotes thermal conductivity of the user's wrist tissue and may be a predetermined value commonly defined for a plurality of users, or may be a value defined differently according to an individual user's characteristics. In this case, the user's wrist tissue may include muscles, fat, bones, skin, and the like of the wrist. $T_{s,upper\ arm}$ denotes surface temperature of the user's upper arm; $T_s$ denotes surface temperature of the user's wrist; $q''_s$ denotes heat flux of the wrist; R denotes a radius of the user's wrist and a value input by the user; $q''_\infty$ denotes heat release from metabolism; $\omega$ denotes blood flow rate; $\rho_b$ denotes blood density; $c_{p,b}$ denotes specific heat at constant pressure of blood and may be a predetermined value commonly defined for a plurality of users; and $I_0(\sqrt{a}\cdot R)$ and $I_1(\sqrt{a}\cdot R)$ denote a Bessel function which is a solution of a heat transfer differential equation.

$h_{eff}$ denotes an integrated convection coefficient, and may be expressed as a sum of the convection coefficient $h_{convention}$ of ambient air surrounding the wrist, the radiation coefficient $h_{radiation}$ of the wrist, and the evaporation coefficient $h_{evaporation}$ of the wrist, and may be obtained based on the skin heat flux $q''_s$ at the wrist, the surface temperature $T_s$ of the user's wrist, and ambient air temperature $T_\infty$ surrounding the apparatus 500 for estimating body temperature.

$T_\infty$ denotes the ambient air temperature surrounding the apparatus 500 for estimating body temperature. For example, $T_\infty$ may be received from an external device. For example, when the apparatus 500 for estimating body temperature and the user are present in an indoor space, a temperature value measured by an indoor thermometer may be received from the external device, and when the apparatus 500 for estimating body temperature and the user are present in an outdoor space, weather forecast information from the weather center and the like may be received from the external device. In another example, $T_\infty$ may be measured by a separate temperature sensor included in the sensor part 510 of the apparatus 500 for estimating body temperature.

As described above, the core body temperature may be estimated with improved accuracy by additionally measuring the surface temperature of the user's upper arm and by using the measured surface temperature in estimating the core body temperature.

Figure 6:
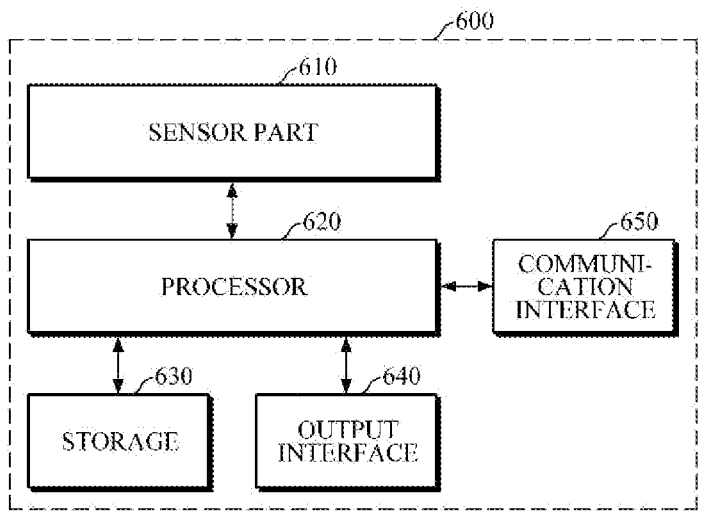
FIG. 6 is a block diagram illustrating an apparatus for estimating body temperature according to yet another example embodiment of the present disclosure.

FIG. 6 is a block diagram illustrating an apparatus for estimating body temperature according to yet another example embodiment of the present disclosure.

Referring to FIG. 6, an apparatus 600 for estimating body temperature may include a sensor part 610, a processor 620, a storage 630, an output interface 640, and a communication interface 650.

The sensor part 610 may include the sensor part 110 of FIG. 1 and/or the sensor part 510 of FIG. 5. The processor 620 may include the processor 120 of FIG. 1 and/or the processor 520 of FIG. 5.

The storage 630 may store information related to estimating core body temperature. For example, the storage 630 may store surface temperature of a user's wrist, surface temperature of a thermally conductive material, surface temperature of the user's upper arm, the user's PPG signal, the user's heart rate, age, stature, and weight, thermal conductivity of the user's wrist tissue, a radius of the user's wrist, blood density, specific heat at constant pressure of blood, a blood flow rate, convection coefficient of blood, ambient air temperature surrounding the user's wrist, as well as processing results of the processor 720, such as skin heat flux of the user's wrist, the user's blood pressure, cardiac output, blood flow rate, the user's metabolism, the user's central wrist temperature, heat flux in the user's wrist, mean temperature of blood, temperature of the blood vessel wall, core body temperature according to distance from the wrist, and the like.

The storage 630 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 640 may provide the processing results of the processor 620 for a user. In particular, the output interface 640 may include a display device. For example, the output interface 640 may display an estimated body temperature value of the processor 620 on the display device. In this case, if the estimated body temperature value falls outside a preset normal range, the output interface 640 may provide the user with warning information by changing color, line thickness, etc., or displaying the abnormal value along with the normal range, so that the user may easily recognize the abnormal value.

Further, along with or without the visual output displayed on the display device, the output interface 640 may provide an estimated core body temperature value for the user in a non-visual manner by voice, vibrations, tactile sensation, and the like using an audio output module such as a speaker, or a haptic module and the like.

The display device may include a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch. The audio module may convert a sound into an electrical signal or vice versa. The audio module may output the sound via a speaker and/or a headphone of another electronic device directly or wirelessly connected to the apparatus for estimating body temperature. The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

An example of displaying the estimated body temperature value by the output interface 640 will be described below with reference to FIGS. 7A and 7B.

Figure 7A:
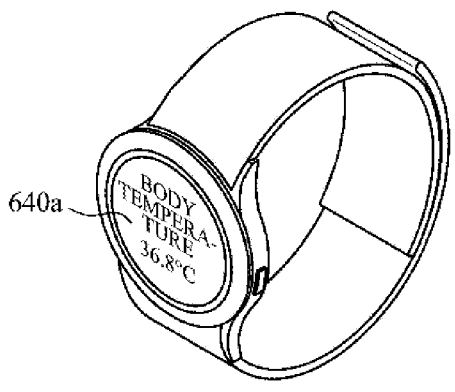
FIGS. 7A and 7B are diagrams illustrating an output interface according to an example embodiment of the present disclosure.
Figure 7B:
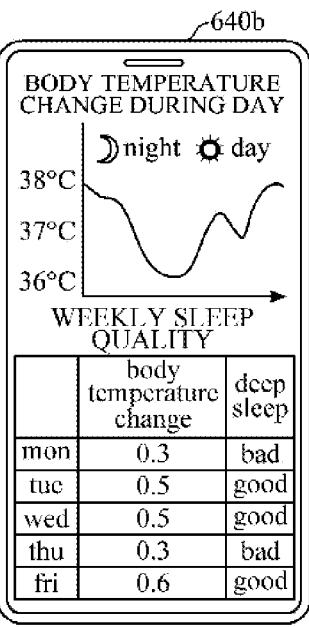

FIGS. 7A and 7B are diagrams illustrating an output interface according to an example embodiment of the present disclosure. Referring to FIGS. 7A and 7B, estimated core body temperature values are displayed on output interfaces 640a and 640b.

For example, as illustrated in FIG. 7A, the output interface 640a may be disposed on a front surface of a wearable device to display the estimated body temperature value. In another example, as illustrated in FIG. 7B, the output interface 640b is disposed on a front surface of a smart device to display the estimated body temperature value, body temperature change during a day, sleep quality related to the estimation of body temperature, and the like. In particular, by interworking with an additional external electronic device, e.g., a wristwatch-type wearable device and an ear wearable device, the smart device may display a core body temperature value, which is estimated based on data measured by a sensor of the additional external electronic device, on the output interface 640b. However, the method of outputting the estimated body temperature value by the output interfaces 640a and 640b are not limited thereto and may be changed variously.

The communication interface 650 may communicate with an external device to transmit and receive various data, related to estimating the core body temperature, to and from the external device. The external device may include an information processing device such as a smartphone, a tablet PC, a desktop computer, a laptop computer, and the like. For example, the communication interface 650 may transmit a body temperature estimation result to the external device, such as a user's smartphone and the like, so that the user may manage and monitor the estimation result by using a device having a relatively high performance.

The communication interface 650 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, this is merely exemplary and is not intended to be limiting.

Figure 8:
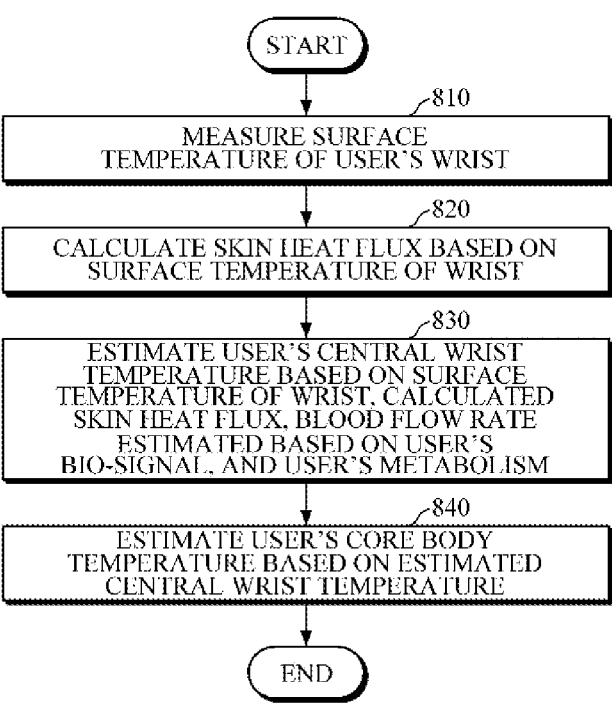
FIG. 8 is a flowchart illustrating a method of estimating body temperature according to an example embodiment of the present disclosure.

FIG. 8 is a flowchart illustrating a method of estimating body temperature according to an example embodiment of the present disclosure. The method of FIG. 8 is an example of a method of estimating body temperature performed by the apparatuses 100 and 600 for estimating body temperature according to the embodiments of FIG. 1 or FIG. 6, which are described above in detail, and thus will be briefly described below.

First, the apparatus for estimating body temperature may measure surface temperature of a user's wrist in operation 810. In particular, the apparatus for estimating body temperature may measure surface temperature of the user's wrist and may include a thermistor, but is not limited thereto. A detailed description thereof will be omitted.

Then, the apparatus for estimating body temperature may calculate skin heat flux based on the surface temperature of the wrist in operation 820. In particular, the apparatus for estimating body temperature may calculate the skin heat flux at the user's wrist based on the measured surface temperature of the user's wrist. For example, the apparatus for estimating body temperature may calculate the skin heat flux of the user based on a value obtained by subtracting, from the surface temperature of the user's wrist, which is measured by the first temperature sensor, the surface temperature of the thermally conductive material which is measured by the second temperature sensor. A detailed description thereof will be omitted.

Subsequently, the apparatus for estimating body temperature may estimate the user's central wrist temperature based on the surface temperature of the wrist, the calculated skin heat flux, a blood flow rate estimated based on a user's bio-signal, and the user's metabolism in operation 830.

In particular, the apparatus for estimating body temperature may estimate the user's blood flow rate based on the measured PPG signal. For example, the apparatus for estimating body temperature may estimate blood pressure and/or cardiac output of the user, and may estimate the user's blood flow rate based on the estimated blood pressure and/or cardiac output.

Based on the user's heart rate, age, stature, weight, etc., the apparatus for estimating body temperature may estimate heat release from metabolism in the user's body.

In particular, based further on thermal conductivity of the user' wrist tissue, the radius of the wrist, blood density, and specific heat at constant pressure of blood, the apparatus for estimating body temperature may estimate the user's central wrist temperature.

Next, the apparatus for estimating body temperature may estimate the user's core body temperature based on the estimated central wrist temperature in operation 840. Based on the user's central wrist temperature, heat flux in the wrist, arterial blood pressure, blood flow rate, and specific heat at constant pressure of blood, the apparatus for estimating body temperature may estimate the core body temperature according to distance from the wrist.

Based on the convection coefficient of blood, mean temperature of blood, and temperature of the blood vessel wall, the apparatus for estimating body temperature may calculate the heat flux in the wrist.

Figure 9:
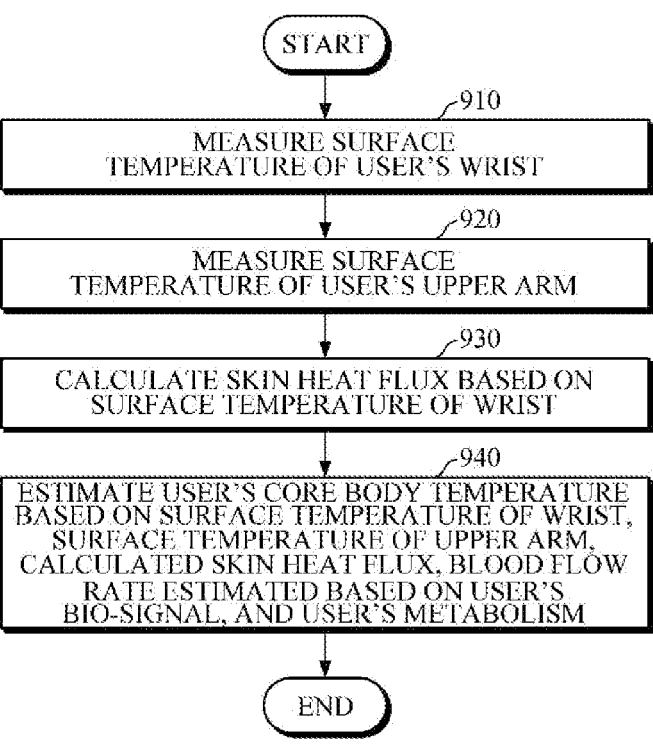
FIG. 9 is a flowchart illustrating a method of estimating body temperature according to another example embodiment of the present disclosure.

FIG. 9 is a flowchart illustrating a method of estimating body temperature according to another example embodiment of the present disclosure. The method of FIG. 9 is an example of a method of estimating body temperature performed by the apparatuses 500 and 600 for estimating body temperature according to the embodiments of FIG. 5 or FIG. 6, which are described above in detail, and thus will be briefly described below.

First, the apparatus for estimating body temperature may measure surface temperature of a user's wrist in operation 910. In particular, the apparatus for estimating body temperature may measure surface temperature of the user's wrist by using a thermistor.

Then, the apparatus for estimating body temperature may measure surface temperature of the user's upper arm in operation 920. In particular, the apparatus for estimating body temperature may calculate the surface temperature of the user's upper arm by using a patch type temperature sensor.

Subsequently, the apparatus for estimating body temperature may calculate skin heat flux based on the surface temperature of the wrist in operation 930. For example, the apparatus for estimating body temperature may calculate the skin heat flux of the user by subtracting the surface temperature of the user's wrist, which is measured by the first temperature sensor, and the surface temperature of the thermally conductive material which is measured by the second temperature sensor.

Operation 930 may be performed prior to operation 920, or operations 920 and 930 may be performed concurrently.

Next, the apparatus for estimating body temperature may estimate the user's core body temperature in operation 940 based on the surface temperature of the wrist, the surface temperature of the upper arm, the calculated skin heat flux, the blood flow rate estimated based on the user's bio-signal, and the user's metabolism.

In this case, based further on ambient air temperature surrounding the user's wrist, the apparatus for estimating body temperature may estimate the user's core body temperature.

Figure 10:
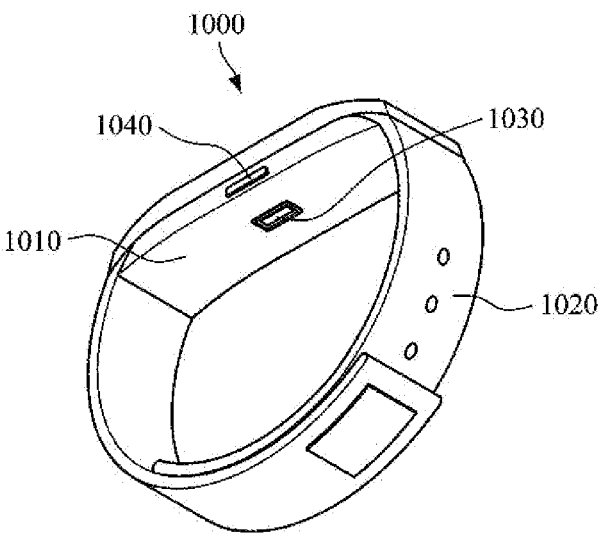
FIG. 10 is a diagram illustrating a wearable device according to an example embodiment of the present disclosure.

FIG. 10 is a diagram illustrating a wearable device according to an example embodiment of the present disclosure. Referring to FIG. 10, the electronic device may be implemented as a smart watch-type wearable device 1000, which includes a main body 1010 and a wrist strap 1020.

The main body 1010 may be formed in various shapes. A battery may be embedded in the main body 1010 and/or the strap 1020 to supply power to various components of the wearable device. The strap 1020 may be connected to both ends of the main body to allow the main body to be worn on a user's wrist, and may be flexible so as to be wrapped around the user's wrist. The strap 1020 may be composed of a first strap and a second strap which are separated from each other. One ends of the first strap and the second strap are connected to both sides of the main body 1010, and the other ends thereof may be connected to each other via a fastening means. In this case, the connecting means may be formed as magnetic fastening, Velcro fastening, pin fastening, and the like, but is not limited thereto. Further, the strap 1020 is not limited thereto, and may be integrally formed as a non-detachable band.

The main body 1010 may include an apparatus for estimating body temperature. A sensor 1030, a processor, a display device, an output interface, a storage, and a communication interface may be mounted in the apparatus for estimating body temperature. However, some of the display device, the output interface, the storage, and the communication interface may be omitted.

The sensor 1030 may include a first temperature sensor disposed at a lower end of a thermally conductive material and sensing surface temperature of an object, and a second temperature sensor disposed at an upper end of the thermally conductive material and sensing surface temperature of the thermally conductive material. The sensor 1030 may be disposed on a rear surface of the main body 1010, so that when the main body 101 is worn on the user's wrist, the sensor 1030 may come into contact with an upper part of the wrist to obtain data for measuring core body temperature from the wrist.

A manipulator 1040 may be formed on a side surface of the main body 1010. The manipulator 1040 may receive a user's control command and may transmit the received command to the processor. In addition, the manipulator 1040 may have a power button to turn on/off the wearable device 1000.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating body temperature, the apparatus comprising:
   a first temperature sensor configured to measure a skin surface temperature at a measurement point of a user;
   a thermally conductive material on the first temperature sensor;
   a second temperature sensor configured to measure a surface temperature of the thermally conductive material; and a processor configured to:
      calculate skin heat flux based on the skin surface temperature and the surface temperature of the thermally conductive material,
      estimate an amount of heat that is released from a body of the user based on at least one of a heart rate, an age, a stature, and a weight of the user, estimate a centroid temperature at the measurement point of the user based on the skin surface temperature at the measurement point, and the calculated skin heat flux, and the estimated amount of heat that is released from the body of the user, and
      estimate a core body temperature of the user based on the estimated centroid temperature at the measurement point.

2. The apparatus of claim 1, wherein at least one of the first temperature sensor and the second temperature sensor is a thermistor.

3. The apparatus of claim 1, wherein the processor is further configured to calculate the skin heat flux by subtracting the surface temperature of the thermally conductive material, from the skin surface temperature at the measurement point of the user.

4. The apparatus of claim 1, further comprising a photoplethysmography (PPG) sensor configured to measure a PPG signal from the user,
   wherein the processor is further configured to estimate blood pressure of the user based on the measured PPG signal, estimate a blood flow rate of the user based on the estimated blood pressure, and estimate the centroid temperature at the measurement point of the user further based on the blood flow rate of the user.

5. The apparatus of claim 1, wherein the processor is further configured to estimate the centroid temperature at the measurement point of the user based further on thermal conductivity of a skin tissue of the user, and a radius of a body part at the measurement point of the user.

6. The apparatus of claim 1, wherein the measurement point is located at a wrist of the user, and the processor is further configured to estimate the core body temperature based on a length of an arm of the user, the centroid temperature of the wrist, a heat flux in the wrist, an arterial blood pressure, and a blood flow rate.

7. The apparatus of claim 6, wherein the processor is further configured to calculate the heat flux in the wrist based on a convection coefficient of blood, a mean temperature of blood, and a temperature of a blood vessel wall.

8. The apparatus of claim 1, further comprising a display configured to provide the user with the estimated core body temperature of the user.

9. The apparatus of claim 1, wherein the measurement point is a first measurement point, and the apparatus further comprises a third temperature sensor configured to measure a skin surface temperature at a second measurement point of the user,
   wherein the processor is further configured to estimate the core body temperature further based on the skin surface temperature at the second measurement point of the user.

10. The apparatus of claim 1, wherein the processor is further configured to estimate the core body temperature further based on an ambient air temperature.

11. A wearable device configured to be worn around a wrist of a user, the wearable device comprising:
   a first contact-type temperature sensor and a second contact-type temperature sensor that are disposed apart from each other, via a thermally conductive layer provided between the first contact-type temperature sensor and the second contact-type temperature sensor; and a processor configured to:

control the first contact-type temperature sensor to measure a skin surface temperature of the wrist;

control the second contact-type temperature sensor to measure a temperature of the thermally conductive layer;

calculate a skin heat flux based on change between the skin surface temperature of the wrist and the temperature of the thermally conductive layer;

calculate a heat flux in the wrist based on a convection coefficient of blood, a mean temperature of blood, and a temperature of a blood vessel wall;

estimate a centroid temperature of the wrist based on the skin surface temperature of the wrist and the skin heat flux; and estimate a core body temperature of the user based on the centroid temperature of the wrist, and a length of an arm of the user.

12. A method of estimating body temperature, the method comprising:

measuring, using a first temperature sensor, a skin surface temperature at a measurement point of a user;

measuring, using a second temperature sensor, a surface temperature of a thermally conductive material, the thermally conductive material being on the first temperature sensor;

calculating a skin heat flux based on the skin surface temperature and the surface temperature of the thermally conductive material;

estimating a centroid temperature at the measurement point based on the skin surface temperature at the measurement point, and the calculated skin heat flux, wherein the estimating of the centroid temperature at the measurement point comprises estimating an amount of heat that is released from a body of the user based on at least one of a heart rate, an age, a stature, and a weight of the user; and estimating a core body temperature of the user based on the estimated centroid temperature at the measurement point.

13. The method of claim 12, wherein the calculating the skin heat flux comprises calculating the skin heat flux by subtracting the surface temperature of the thermally conductive material from the skin surface temperature.

14. The method of claim 12, wherein the estimating of the centroid temperature at the measurement point comprises:

measuring a photoplethysmography (PPG) signal from the user, estimating blood pressure of the user based on the measured PPG signal;

estimating a blood flow rate based on the estimated blood pressure of the user, and estimating the centroid temperature further based on the blood flow rate.

15. The method of claim 12, wherein the estimating the centroid temperature at the measurement point comprises estimating the centroid temperature at the measurement point based further on thermal conductivity of a skin tissue of the user and a radius of a body part at the measurement point of the user.

16. The method of claim 12, wherein the measurement point is located at a wrist of the user, and the estimating the core body temperature of the user comprises estimating the centroid temperature of the wrist based on a length of an arm of the user, the centroid temperature of the wrist, a heat flux in the wrist, an arterial blood pressure, and a blood flow rate.

17. The method of claim 16, wherein the estimating the core body temperature of the user comprises calculating the heat flux in the wrist based on a convection coefficient of blood, a mean temperature of blood, and a temperature of a blood vessel wall.

18. A wearable device configured to be worn around a wrist of a user, the wearable device comprising:

a first temperature sensor configured to measure a skin surface temperature at a measurement point of a user;

a thermally conductive material on the first temperature sensor;

a second temperature sensor configured to measure a surface temperature of the thermally conductive material;

a photoplethysmography (PPG) sensor configured to measure a PPG signal from the user; and a processor configured to:

calculate skin heat flux based on the skin surface temperature and the surface temperature of the thermally conductive material, calculate a heat flux in the wrist based on a convection coefficient of blood, a mean temperature of blood, and a temperature of a blood vessel wall, estimate blood pressure of the user based on the measured PPG signal, estimate a blood flow rate of the user based on the estimated blood pressure, estimate a centroid temperature at the measurement point of the user based on the skin surface temperature, the skin heat flux, and the blood flow rate, and estimate a core body temperature of the user based on the centroid temperature at the measurement point.

19. The wearable device of claim 18, wherein the processor is further configured to calculate the skin heat flux by subtracting the surface temperature of the thermally conductive material, from the skin surface temperature at the measurement point of the user.

* * * * *